(12) United States Patent
Mano et al.

(10) Patent No.: US 7,749,692 B2
(45) Date of Patent: Jul. 6, 2010

(54) TISSUE PRESERVATION METHOD COMPRISING CONTACTING TISSUE WITH A SOLUTION OF NANOBUBBLES AND SALT

(75) Inventors: Yoshihiro Mano, Tokyo (JP); Kenji Sato, Tokyo (JP); Yuichiro Cho, Chiba (JP); Kaneo Chiba, Miyagi (JP)

(73) Assignees: National University Corporation Tokyo Medical and Dental University, Tokyo (JP); REO Laboratory Co., Ltd., Miyagi (JP)

( * ) Notice: Subject to any disclaimer, the term of this patent is extended or adjusted under 35 U.S.C. 154(b) by 516 days.

(21) Appl. No.: 11/711,396

(22) Filed: Feb. 27, 2007

(65) Prior Publication Data

US 2008/0057486 A1    Mar. 6, 2008

(30) Foreign Application Priority Data

Sep. 6, 2006   (JP) .............................. 2006-241189

(51) Int. Cl.
*A01N 1/00* (2006.01)
(52) U.S. Cl. ....................................................... 435/1.1
(58) Field of Classification Search ........................ None
See application file for complete search history.

(56) References Cited

U.S. PATENT DOCUMENTS

| | | | |
|---|---|---|---|
| 6,649,145 B2 * | 11/2003 | McGrath et al. | 424/45 |
| 6,689,262 B2 * | 2/2004 | Senkiw | 204/278.5 |
| 2007/0286795 A1 * | 12/2007 | Chiba et al. | 423/580.1 |

FOREIGN PATENT DOCUMENTS

| | | | |
|---|---|---|---|
| JP | 2005-246294 | | 9/2005 |
| WO | WO 2005/084786 A1 * | | 9/2005 |

OTHER PUBLICATIONS culture. (n.d.). Dictionary.com Unabridged (v1.1). Retrieved Sep. 16, 2009, from Dictionary.com website: http://dictionary.reference.com/browse/culture.*
Bowdler et al. "The time course of red cell lysis in hypotonci electrolyte solutions", J. Physiol. 201 : 437-452 (1969).*

* cited by examiner

*Primary Examiner*—Sandra E Saucier
(74) *Attorney, Agent, or Firm*—Carmody & Torrance LLP

(57) ABSTRACT

An object of the invention is to provide a tissue preservation solution that has excellent tissue-preserving ability and is useful in the field of medicine, medical experiment, etc. Thus, the invention relates to a tissue preservation solution including oxygen nanobubbles.

8 Claims, 4 Drawing Sheets

FIG. 1

Rat 1 : Left Vagus Nerve

| L1 |
|---|

← Central Side      Peripheral Side →

Rat 1 : Right Vagus Nerve

| R1 |
|---|

← Central Side      Peripheral Side →

Rat 2 : Left Vagus Nerve

| L2 | C-A1 | NB-A1 | DMEM-A1 | NCM-A1 |
|---|---|---|---|---|

← Central Side      Peripheral Side →

Rat 2 : Right Vagus Nerve

| R2 | C-B1 | NB-B1 | DMEM-B1 | NCM-B1 |
|---|---|---|---|---|

← Central Side      Peripheral Side →

Rat 3 : Left Vagus Nerve

| L3 | C-A3 | NB-A3 | DMEM-A3 | NCM-A3 |
|---|---|---|---|---|

← Central Side      Peripheral Side →

Rat 3 : Right Vagus Nerve

| R3 | C-B3 | NB-B3 | DMEM-B3 | NCM-B3 |
|---|---|---|---|---|

← Central Side      Peripheral Side →

Rat 4 : Left Vagus Nerve

| L4 | C-A7 | NB-A7 | DMEM-A7 | NCM-A7 |
|---|---|---|---|---|

← Central Side      Peripheral Side →

Rat 4 : Right Vagus Nerve

| R4 | C-B7 | NB-B7 | DMEM-B7 | NCM-B7 |
|---|---|---|---|---|

← Central Side      Peripheral Side →

TISSUE PRESERVATION METHOD COMPRISING CONTACTING TISSUE WITH A SOLUTION OF NANOBUBBLES AND SALT

BACKGROUND OF THE INVENTION

1. Field of the Invention

The present invention relates to a tissue preservation solution that is useful in the field of medicine, medical experiment, etc.

2. Description of the Related Art

In the medicine that is making rapid advances in recent years, the importance of tissue (as well as organ and cell, hereinafter the same shall apply) transplant increases, and the advances are supported by the progress, for example, in immunosuppressive agents and tissue preservation technology. In the tissue transplant, it is ideal that the tissue removed from a donor be transplanted immediately to a recipient, but it is not always transplanted immediately. Thus, it is extremely important how the removed tissue is to be preserved, and currently a better tissue preservation solution has been desired.

In recent years, attention has been paid to various bioactive effects of water that contains nanobubbles of oxygen in large amount (oxygen-nanobubble water) on living organisms. For example, oxygen-nanobubble water improves adaptability of fish and shellfish to environmental change, or restores a debilitated individual quickly (See, for example, Japanese Patent Application Laid-Open UP-A) No. 2005-246294). Nanobubbles are ultrafine bubbles with a diameter of 1 µm or less, and are typically generated in the process where microbubbles (minute bubble with a diameter of 50 µm or less) shrink. Since nanobubbles are self-pressurized by the action of surface tension, they are completely dissolved rapidly. Thus, the lifetime was considered to be short in general. However, it is reported that in the case where nanobubbles are coated with shell by a surfactant, or in the case where they are subjected to electrostatic repulsion due to surface charging, even bubbles in nano-order can exist for a certain period. Especially, nanobubbles stabilized due to charging effect retain properties as bubble; thus various applications, such as direct action to organisms at cellular level, are expected (See, for example, JP-A No. 2005-246294).

BRIEF SUMMARY OF THE INVENTION

An object of the invention is to solve the conventional problems and to achieve the following objects. Specifically, an object of the invention is to provide a tissue preservation solution that has excellent tissue-preserving ability and is useful in the field of medicine, medical experiment, etc.

In order to solve the problems, inventors of the present invention have investigated vigorously and have found the following experiences or discoveries. Specifically, they have found that oxygen-nanobubble water can exhibit tissue-preserving effect similar to, or more than the conventional tissue culture mediums such as Dulbecco's modified Eagle medium (DMEM) and neuron culture medium (NCM).

As described above, it has been known that oxygen-nanobubble water has various bioactive effects on living organisms. For example, it improves adaptability of fish and shellfish to environmental change, or restores a debilitated individual quickly. Thus, the oxygen-nanobubble water is attracting attention. In addition, recently a method for producing oxygen-nanobubble water has been established that can maintain nanobubbles stably for a long time (See, for example, JP-A No. 2005-246294).

Previously, however, it has not been known that the oxygen-nanobubble water can exhibit tissue-preserving effect similar to, or more than the conventional tissue culture mediums, and that therefore, the oxygen-nanobubble water can be suitably utilized as an excellent tissue preservation solution in the field of medicine, medical experiment, etc., which was newly found by the inventors of the present invention.

Accordingly, the invention is based on the above-mentioned findings by the inventors of the present invention. The means for solving the problems is a tissue preservation solution including oxygen nanobubbles.

The invention can solve the conventional problems and can provide a tissue preservation solution that has excellent tissue-preserving ability and is useful in the field of medicine, medical experiment, etc.

BRIEF DESCRIPTION OF THE SEVERAL VIEWS OF THE DRAWINGS

FIG. 1 is a schematic view showing each part of rat vagus nerve tissue and each preservation method that were used in Example 1.

Figure 2:
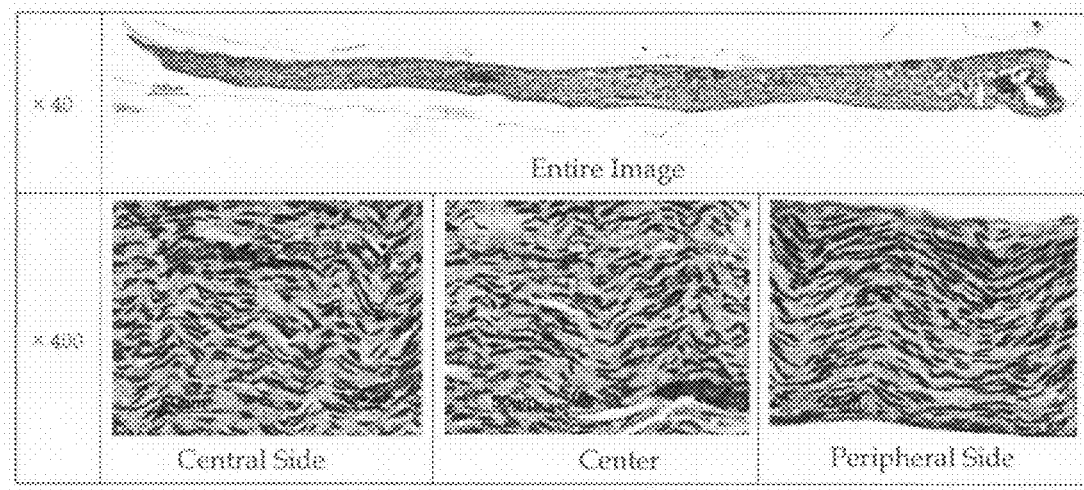
FIG. 2 is optical microscope images (H.E. staining: ×400) of a normal control vagus nerve tissue (left side: L1).

DETAILED DESCRIPTION OF THE INVENTION (Tissue Preservation Solution)

The tissue preservation solution of the invention comprises oxygen nanobubbles.

<Oxygen-Nanobubble Water>

In the invention, "oxygen nanobubble" refers to a bubble which comprises oxygen and which has a nano-order diameter (1 µm or less). "Oxygen-nanobubble water" refers to an aqueous solution that comprises oxygen wherein the oxygen exists as the oxygen nanobubble. Specifically, the oxygen-nanobubble water is a preferable aspect of the tissue preservation solution of the invention.

Oxygen nanobubbles present in oxygen-nanobubble water for use in the tissue preservation solution of the invention may have a variety of bubble diameters. Among them, the bubble diameter is preferably 200 nm or less, more preferably 100 nm or less and most preferably less than 10 nm. Oxygen nanobubbles with a diameter of 100 nm or less are advantageous in that there is less possibility for incorporation of electrolytes or foreign substances. Oxygen nanobubbles with a diameter less than 10 nm are further advantageous in that incorporation of many foreign substances including viruses can be prevented.

The bubble diameter of the oxygen nanobubble can be adjusted to a desired size using, for example, a reverse osmosis membrane. The bubble diameter of the oxygen nanobubble can be measured with, for example, a dynamic light scattering equipment.

The oxygen concentration of the oxygen-nanobubble water is preferably saturated level. It is important that the oxygen nanobubbles be dissolved in an aqueous solution sufficiently.

The salt concentration, pH, and hardness of the oxygen-nanobubble water are not particularly limited and can be appropriately selected depending on the application. For example, each of them can be adjusted to a desired degree during the production process of oxygen-nanobubble water described below or after the production of oxygen-nanobubble water.

—Other Element—

The oxygen-nanobubble water may comprise other elements than the oxygen nanobubbles as necessary. Specific examples of the other element are not particularly limited and can be appropriately selected depending on the application, including, for example, iron, manganese, and salts.

—Production—

The oxygen-nanobubble water can be produced by any method without limitation and the method can be appropriately selected depending on the application. For example, the oxygen-nanobubble water can be produced by the production method disclosed in JP-A No. 2005-246294. The production method disclosed in the gazette is preferable since it can produce oxygen-nanobubble water in which oxygen nanobubbles exist stably and do not disappear from the aqueous solution over a long period of several months or more.

The salt concentration of the aqueous solution used in the production process of the oxygen-nanobubble water is preferably 0.2% by mass to 3.0% by mass, and more preferably 0.8% by mass to 1.2% by mass. When the salt concentration is within the range of from 0.8% by mass to 1.2% by mass, nanobubbles (core of gas) can be produced easily; thus it is advantageous in that production efficiency of the oxygen-nanobubble water is excellent. The salt concentration can be measured using, for example, a known instrument for measuring salt concentration.

It is considered that the pH and hardness of the aqueous solution used in the production process of the oxygen-nanobubble water does not affect the production efficiency of oxygen nanobubbles as greatly as does the salt concentration. Typically, the pH is preferably 7 to 8, and the hardness is preferably 20 to 30. The pH and hardness can be measured using, for example, a known instrument for measuring pH and a known instrument for measuring hardness, respectively.

In the production process of the oxygen-nanobubble water, iron, manganese, and/or salts can be preferably added.

Specifically, oxygen microbubbles of 50 µm or less are produced using hard water (groundwater) with a salt concentration of 1.0% by mass as a raw material. Then, by rapidly collapsing or crushing the oxygen microbubbles, oxygen-nanobubble water can be produced. Further, purified oxygen-nanobubble water (salt content: 0% by mass), "Naga no shizuku" (drips of Naga) (manufactured by NAGA Co., Ltd.), can be prepared by passing the resulting oxygen-nanobubble water through a reverse osmosis membrane of 10 nm. "Naga no shizuku" is drinking water approved by the Ministry of Health, Labour and Welfare. Meanwhile, oxygen-nanobubble water with a salt concentration of 1.0% by mass is oxygen-nanobubble water that is not passed through a reverse osmosis membrane of 10 nm. Varying the mixing ratio of both of the oxygen-nanobubble waters can provide oxygen-nanobubble waters with a salt concentration of from 0% by mass to 1.0% by mass.

The oxygen-nanobubble water prepared as mentioned above may be used as the tissue preservation solution itself, however, for example, the oxygen-nanobubble water may be added to an existing tissue preservation solution, or a tissue preservation solution that includes the oxygen-nanobubble water as an ingredient and has a conventional composition may be prepared. This will further enhance capability to preserve tissues. Since oxygen-nanobubble water is aseptic water and has a high disinfecting ability, it is suitably used for preparing tissue preservation solution by means of such methods. Thus, such tissue preservation solutions as mentioned above that utilize oxygen-nanobubble water in part are also included within the scope of the tissue preservation solution of the invention.

<Tissue>

The object to be preserved in the tissue preservation solution not particularly limited and can be appropriately selected depending on the application. The tissue preservation solution of the invention is also suitable for the preservation of "cell" or "organ".

The "tissue" is not particularly limited and can be appropriately selected depending on the application; examples thereof include epithelial tissues, connective tissues, muscular tissues, and nerve tissues.

The "cell" is not particularly limited and can be appropriately selected depending on the application; examples thereof include epidermal cells, pancreatic parenchymal cells, pancreatic ductal cells, hepatic cells, blood cells, cardiac muscle cells, skeletal muscle cells, osteoblasts, skeletal myoblasts, nerve cells, endothelial cells, pigment cells, smooth muscle cells, fat cells, bone cells, and cartilage cells.

The "organ" is not particularly limited and can be appropriately selected depending on the application; examples thereof include skin, blood vessel, cornea, kidney, heart, liver, umbilical cord, intestine, nerve, lung, placenta, pancreas, brain, peripheral extremities, and retina.

The organism from which the tissue, cell, and organ is derived is not particularly limited and can be appropriately selected depending on the application. The tissues, cells, and organs derived from a mammal are preferable, and tissues, cells, and organs derived from a human are more preferable.

<Use>

The tissue preservation solution may be used without limitation. The tissue preservation solution can be used in the same manner as a conventional tissue preservation solution. For example, the tissue, cell, organ, or the like is removed from a living body, and then it is immersed in the tissue preservation solution for a desired period.

The tissue preservation solution itself can be stored by any method without limitation and the method can be appropriately selected depending on the application.

Since the tissue preservation solution has excellent tissue-preserving ability, it can be suitably utilized, for example, as a tissue preservation solution in the field of medicine, medical experiment, etc.

EXAMPLES

Examples of the invention are illustrated below, but these are not to be construed as limiting the invention.

Example 1

Evaluation of Effect of Oxygen-Nanobubble Water on Tissue Preservation

Oxygen-nanobubble water (REO Laboratory Co., Ltd.), one aspect of the tissue preservation solution of the invention, was prepared with reference to the production method disclosed in JP-A No. 2005-246294. Specifically, oxygen microbubbles of 50 µm or less was produced using hard water (groundwater) with a salt concentration of 1.0% by mass as a raw material. Then, by rapidly collapsing or crushing the oxygen microbubbles, oxygen-nanobubble water was produced.

The effect of the prepared oxygen-nanobubble water on tissue preservation was histologically investigated using rat vagus nerve as a material. Physiological saline and conventional tissue culture medium were used as a control.

<Method>

—Storage/Fixation of Tissue—

Four rats (rats 1 to 4) (Std: Wistar/ST, 10 weeks of age, male, 300 g) were anesthetized with Nembutal, and vagus nerves on both sides (total 8 nerves) were removed using an operation microscope. Next, of the removed vagus nerves, vagus nerves (total two nerves) removed from one rat (rat 1) were used for the following experimental operations without cutting. The vagus nerves (total six nerves), removed from the remaining three rats (rats 2 to 4), were each cut into five pieces.

Immediately after the cutting or removal, the part very near to the central nerve, (L2 to L4, R2 to R4), of each vagus nerve removed from three rats (rats 2 to 4) and the entire vagus nerve removed from the remaining one rat (rat 1), as a normal control vagus nerve tissue, were fixed with Zamboni's fixative (15% picric acid, 4% paraformaldehyde, 0.4 M phosphate buffer, pH 7.4) at 4° C. for one week. Also, the rest of each vagus nerve tissue removed from three rats (rats 2 to 4) was divided and each part of the tissue was stored, starting from the part near to the central nerve, in physiological saline (C), oxygen-nanobubble water (NB), Dulbecco's modified Eagle medium (DMEM), and neuron culture medium (NCM), respectively, at 4° C. (FIG. 1, where left side and right side are represented by A and B, respectively). After 1, 3, or 7 days, each part of the tissue was placed in Zamboni's fixative and fixed at 4° C. for one week. Further, each fixed vagus nerve tissue was embedded using a low melting point-paraffin (52° C.).

Each part of the rat vagus nerve tissue shown in FIG. 1 corresponds to each storage method as follows.

[Storage Method]

L1 to L4, R1 to R4: fixed immediately after the cutting or removal

C-A1, 3, 7, C-B1, 3, 7: stored in physiological saline

NB-A1, 3, 7, NB-B1, 3, 7: stored in oxygen-nanobubble water

DMEM-A1, 3, 7, DMEM-B1, 3, 7: stored in DMEM

NCM-A1, 3, 7, NCM-B1, 3, 7: stored in NCM

[Period of Storage]

A1, B1: stored for 1 day

A3, B3: stored for 3 days

A7, B7: stored for 7 days

—Hematoxylin-Eosin Staining (H. E. Staining)—

Each paraffin-embedded vagus nerve tissue was sliced at 8 µm using a microtome, and then placed on MAS-coated glass slide. Sections were deparaffinized through a xylene series and an alcohol series, and alcohol was removed from deparaffinized sections by rinsing in distilled water for 5 minutes. Then, the nuclei were stained at room temperature for 30 minutes using Mayer's hematoxylin solution. Further, after washing in running water for 15 minutes to blue the nuclei, fiber, stroma, and the like were stained with 10% eosin solution for 5 minutes. Sections were washed in running water for 1 minute, followed by distilled water. Then, excess eosin was removed and sections were dehydrated with an alcohol series, cleared through a xylene series, and then mounted with Entellan neu to prepare H. E. stained tissue specimens (See, for example, Reference Literatures (1) and (2) below).

Next, the prepared H. E. stained tissue specimens were examined using an optical microscope, and the state of the tissue after the storage was evaluated histologically by examining microscopic morphological changes of each vagus nerve tissue (See, for example, Reference Literatures (3) to (8)).

<Results>

Figure 3:
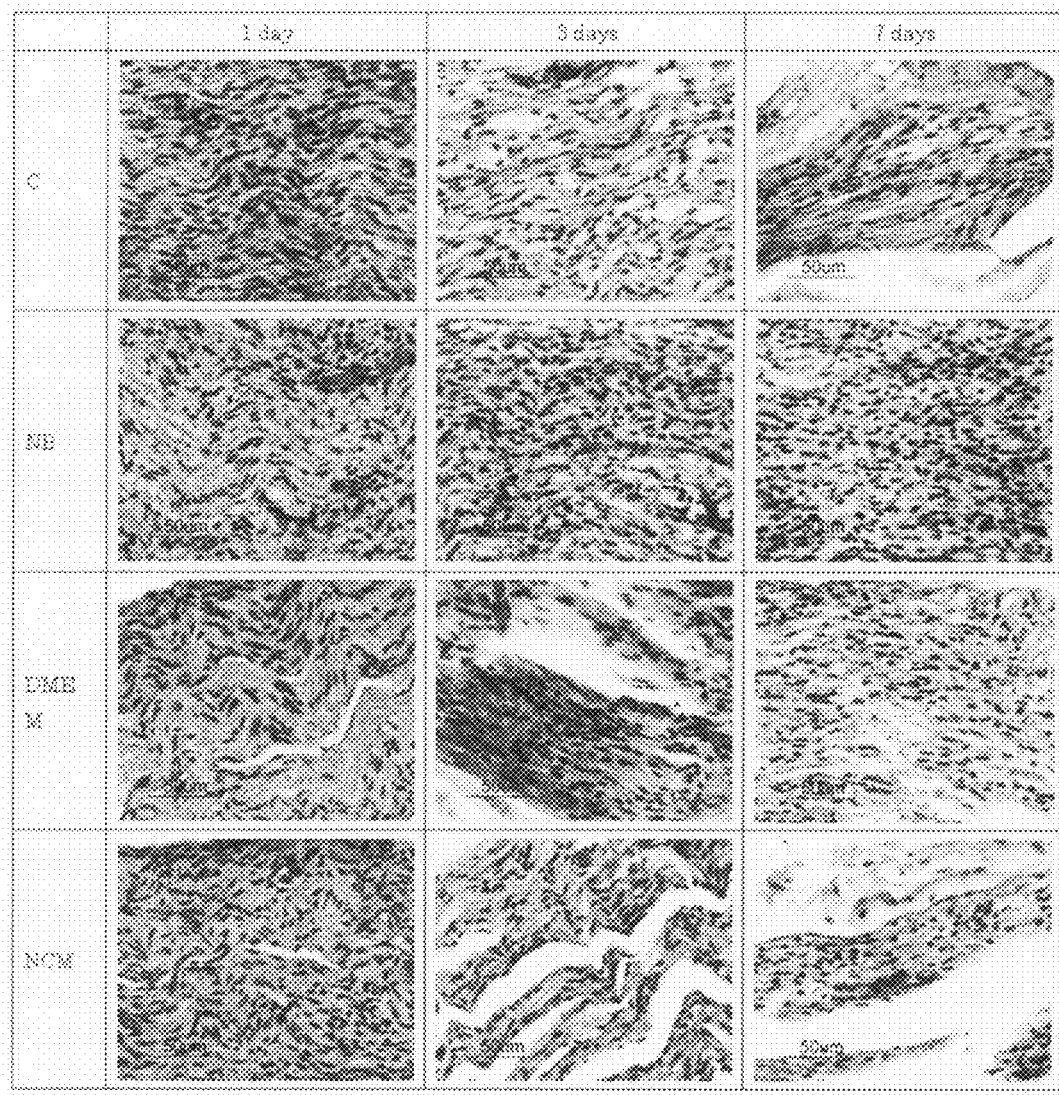
FIG. 3 is optical microscope images (H.E. staining: ×400) of each vagus nerve tissue (left side: parts represented by A).
Figure 4:
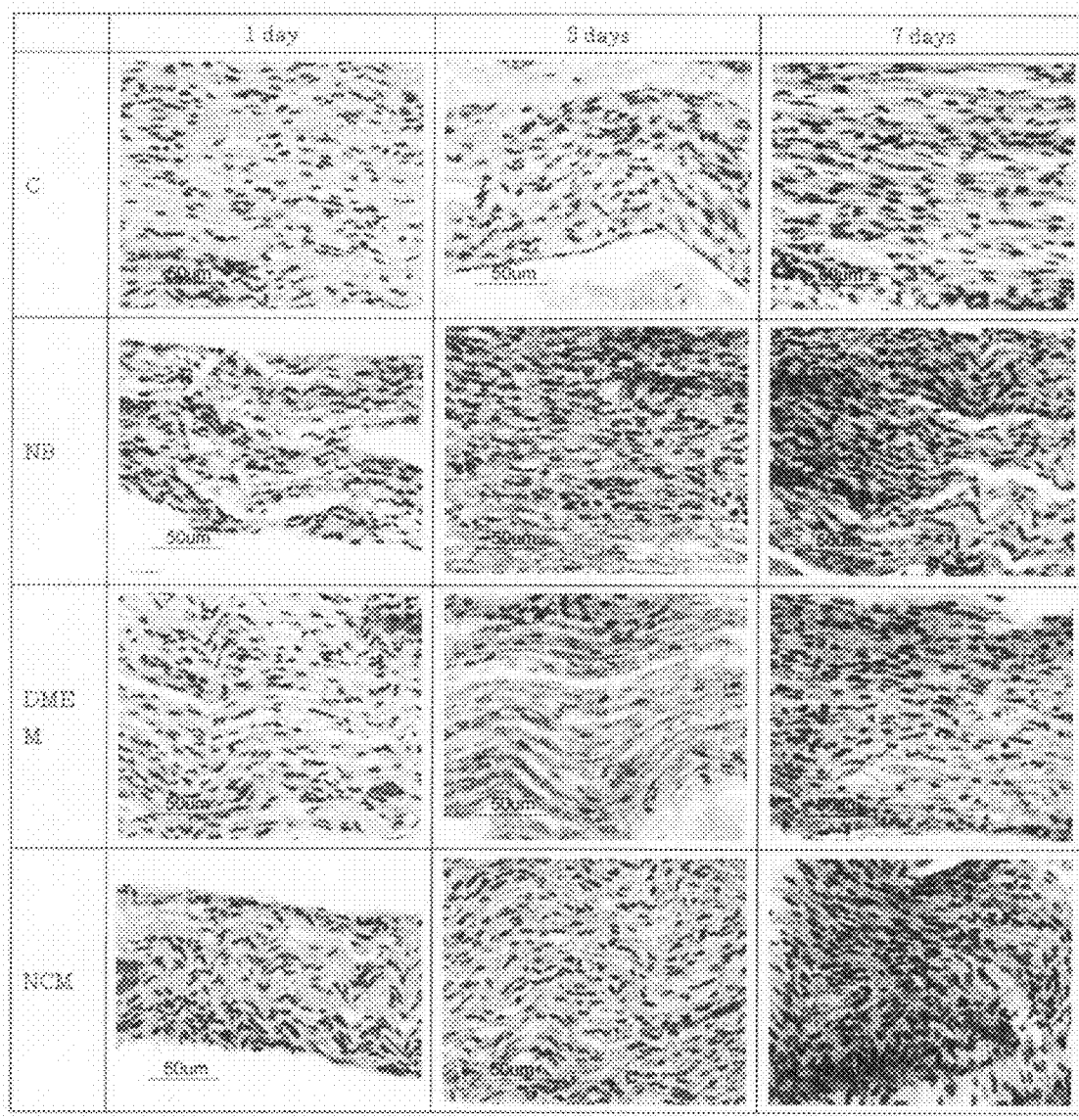
FIG. 4 is optical microscope images (H.E. staining: ×400) of each vagus nerve tissue (right side: parts represented by B).

Results are shown in FIGS. 2 to 4 and Table 1.

For the microscopic morphology of the normal control vagus nerve tissue, histological differences were not observed between central side, center, and peripheral side (FIG. 2). Also, histological differences were not observed between left side and right side, and between individuals.

In the case of storage in physiological saline (C), there was a significant thinning due to the cytoplasmic loss in the vagus nerve tissue stored for 3 days or later. In the case of storage in DMEM, a certain degree of cytoplasmic loss was observed in the vagus nerve tissue stored for 3 days, and there was a significant thinning due to the cytoplasmic loss in the vagus nerve tissue stored for 7 days. In contrast, in the case of storage in oxygen-nanobubble water (NB) or NCM, the tissue were preserved relatively well, and only a mild degree of cytoplasmic loss was observed in the vagus nerve tissue stored for 7 days (FIGS. 3 and 4).

For each vagus nerve tissue, the state of tissue after storage was evaluated histologically according to the following evaluation standards. The results are shown in Table 1.

[Evaluation Standards]

3+: Maintenance of good microscopic morphology

2+: Mild degree of cytoplasmic loss

+: Significant thinning due to the cytoplasmic loss

TABLE 1

| | Storage condition | Storage for 1 day | Storage for 3 days | Storage for 7 days |
|---|---|---|---|---|
| Left side (represented by A) | Physiological saline | 3+ | + | + |
| | Oxygen nanobubble water | 3+ | 2+ | 2+ |
| | DMEM | 3+ | 2+ | + |
| | NCM | 3+ | 2+ | 2+ |
| Right side (represented by B) | Physiological saline | 2+ | + | + |
| | Oxygen nanobubble water | 2+ | 2+ | 2+ |
| | DMEM | 2+ | + | + |
| | NCM | 2+ | 2+ | 2+ |

As shown in results of Table 1, in the case of the vagus nerve tissue stored in oxygen-nanobubble water, there was less thinning due to the cytoplasmic loss in the vagus nerve tissue and the microscopic morphology of the vagus nerve tissue was maintained better, compared to those stored in physiological saline and in DMEM. In addition, the vagus nerve tissue stored in oxygen nanobubble was preserved as well as that stored in NCM. The tissue-preserving ability of each preservation solution used in this Example 1 was in the order of oxygen-nanobubble water≧NCM>DMEM>physiological saline.

The above-mentioned results indicate that the tissue preservation solution of the invention, which comprises oxygen nanobubbles, has excellent tissue-preserving ability, suggesting that it can be applied as a tissue preservation solution in the field of medicine, medical experiment, etc.

[Reference Literature]

Reference literatures in the Examples are as follows.

(1) Shinkichi Akao, Akira Aso, Shinji Adachi, kenichi Anan, Michiko Abe et al. (1997) "Shin senshokuho no subete" (all staining methods), Ishiyaku Publishers, Inc., 3-6

(2) Moe Shimotori (2004) "Functional and histological study of transection and regeneration pattern of vagus nerve" graduation thesis, Tokyo Medical and Dental University (3) Yoshifusa Shimizu, Chizuka Ide, Koki Kawamura, Shigeo Toya, Hideo Togi (1997) "Regeneration and functional rebuilding of the nerves—basic and clical medicine—", Nishimura-Shoten, 227-249

(4) Bray G M, Aguayo A J (1974) "Regeneration of peripheral unmyelinated nerves. Fate of the axonal sprouts which develop after injury", J Anat, 117:517-529

(5) Barbara Young, John W Heath (2001) "Functional Histology A Text and Colour Atlas" 4th edition, Japanese version, Igaku-Shoin, 116-142

(6) Alan Stevens, James Lowe (1999) "Human Histology", translation of the second edition, Nankodo, 77-98

(7) Leslie P Gartner, James L Hiatt (2003) "Color Textbook of Histology" Nishimura-Shoten, 157-187

(8) Leslie P Gartner, James L Hiatt (1999) "Color Atlas of Histology", Japanese version, Medical Sciences International, 126-146

The tissue preservation solution of the invention has good tissue-preserving ability and is thus useful as a tissue preservation solution in the field of medicine, medical experiment, etc.

What is claimed is:

1. A method of preserving a sample of tissue, said method comprising: contacting said tissue with an aqueous solution comprising a) bubbles, which have a diameter of 1 μm or less which comprise oxygen, and b) salt up to 1% by mass, wherein the diameter of the bubbles has been adjusted by passing the aqueous solution of the bubbles through a reverse osmosis membrane, and wherein the salt content of the aqueous solution, after passing through the reverse osmosis membrane, is adjusted by up to 1% by mass.

2. A method according to claim 1, wherein the pH is from 7 to 8.

3. A method according to claim 1, wherein the bubbles have a diameter of 200 nm or less.

4. A method according to claim 1, wherein the bubbles have a diameter of 10 nm or less.

5. A method according to claim 1 wherein the aqueous solution comprises a salt at a concentration of from 0.2% to 1.0% by mass.

6. A method according to claim 5, wherein the pH is from 7 to 8.

7. A method according to claim 6, wherein the bubbles have a diameter of 200 nm or less.

8. A method according to claim 6, wherein the bubbles have a diameter of 10 nm or less.

* * * * *